United States Patent [19]
Eberly

[11] 3,981,794
[45] Sept. 21, 1976

[54] AROMATIZATION PROCESS AND CATALYSTS

[75] Inventor: Paul E. Eberly, Baton Rouge, La.

[73] Assignee: Exxon Research and Engineering Company, Linden, N.J.

[22] Filed: Dec. 9, 1974

[21] Appl. No.: 531,061

Related U.S. Application Data

[63] Continuation-in-part of Ser. No. 395,935, Sept. 16, 1973, abandoned, which is a continuation-in-part of Ser. No. 183,382, Sept. 24, 1971, abandoned.

[52] U.S. Cl. ............................ 208/138; 252/465; 260/673.5
[51] Int. Cl.$^2$ .................. C10G 35/08; C07C 5/30; B01J 23/16
[58] Field of Search ............... 260/673.5, 680, 668; 252/465; 208/138

[56] References Cited
UNITED STATES PATENTS

| | | | |
|---|---|---|---|
| 2,317,683 | 4/1943 | Greensfelder | 260/668 |
| 2,319,948 | 5/1943 | Pitzer | 260/673.5 |
| 2,785,209 | 3/1957 | Schmetterling | 260/668 |
| 2,941,016 | 6/1960 | Schmetterling | 260/673.5 |
| 2,985,596 | 5/1961 | Pitzer | 252/465 |
| 3,586,730 | 6/1971 | Michaels et al. | 260/680 |
| 3,751,497 | 8/1973 | Schwerdtel et al. | 252/465 |

*Primary Examiner*—Delbert E. Gantz
*Assistant Examiner*—J. W. Hellwege
*Attorney, Agent, or Firm*—L. A. Proctor

[57] ABSTRACT

A process for converting hydrocarbons to aromatic compounds comprising contacting a paraffinic or olefinic hydrocarbon feedstream, without added hydrogen, with a catalyst comprising from about 0.05 to about 5% of palladium metal and from about 0.1 up to 2% chromium oxides composited with a high surface area support. A preferred process is one for aromatization of such feeds by contact with a catalyst comprised of from about 0.05 to about 5% of palladium metal, from about 0.1 to less than 2% chromium oxide and up to about 4.5% by weight of an alkali metal oxide incorporated therewith to increase the aromatization activity of the catalyst. Catalysts used in accordance with the present invention comprise compositions which include from about 0.05 to about 5% palladium, from about 0.01 to less than 2% chromium oxides and up to about 4.5% of an alkali metal oxide.

24 Claims, 1 Drawing Figure

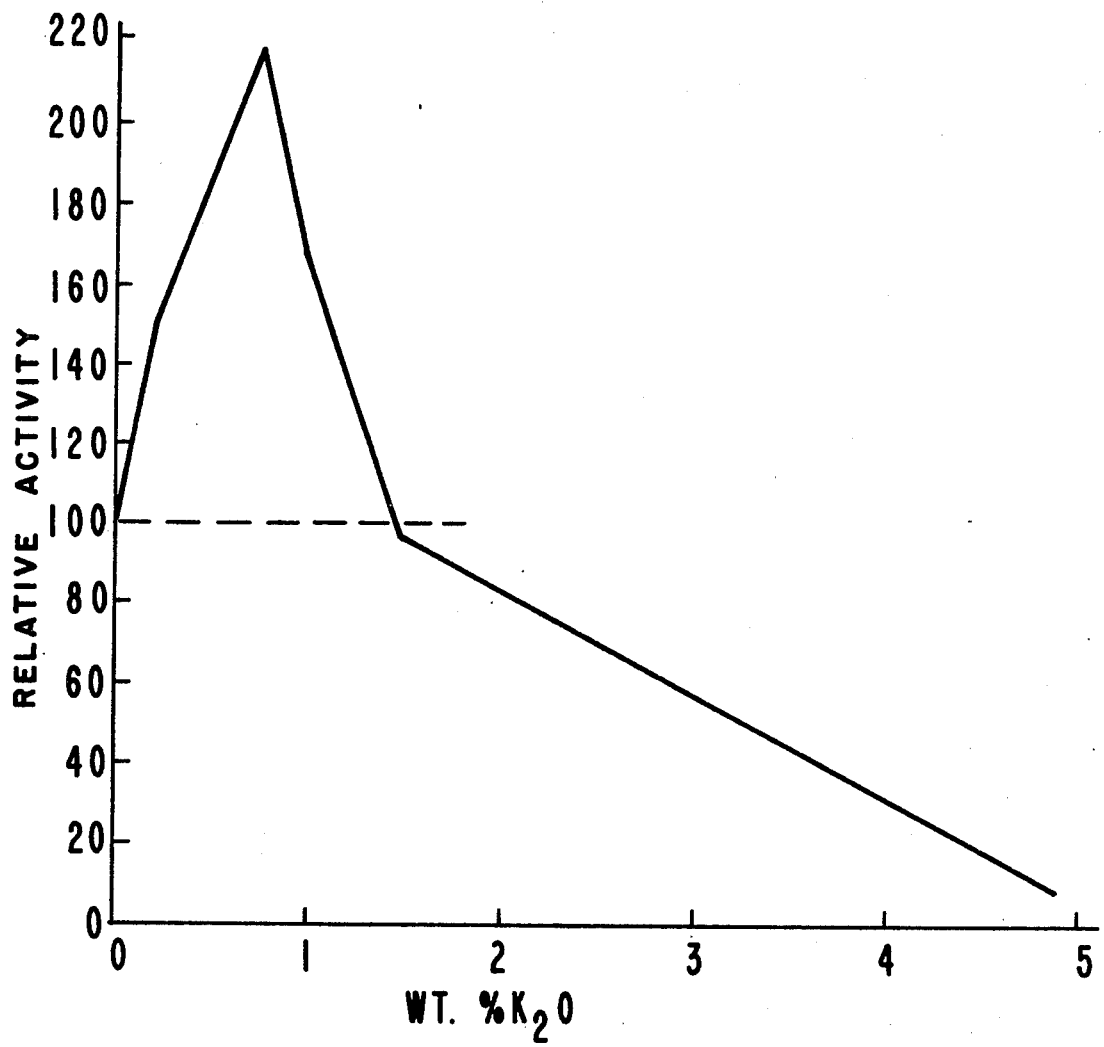

AROMATIZATION PROCESS AND CATALYSTS

RELATED APPLICATIONS

This is a continuation-in-part of U.S. Ser. No. 395,935, filed Sept. 16, 1973, now abandoned, which in turn is a continuation-in-part of U.S. Ser. No. 183,382, filed Sept. 24, 1971, now abandoned.

This invention relates to an improved aromatization process and to novel catalysts therefor. More particularly, this invention relates to processes and catalyst systems which effectively convert paraffins, olefins and diolefins, cycloparaffins, cycloolefins, and mixtures thereof to aromatics.

Many refinery streams are generally blended to produce motor gasoline. The main components of a refinery gasoline pool, howver, are catalytically cracked and virgin naphthas. The light olefins, especially propylene and butylene, are most often separated from these naphtha streams and catalytically polymerized to make gasoline. Nevertheless, these streams still contain a significant amount of higher olefins. These materials can produce smog-forming compounds in internal combustion engines and, as a consequence, can contribute to air pollution. Because of the relatively low octane number of the virgin naphtha component of the refinery gasoline pool, it is generally considered desirable to subject the blended streams to a reforming operation to raise the octane number. In the reforming operation, dehydrogenation, aromatization and isomerization occur. The resulting aromatics and highly branched paraffins which are obtained by catalytic reforming are valuable components for gasoline because of their very high blending octane number. Unfortunately, such reforming catalysts are not particularly effective in converting certain hydrocarbons, particularly olefins and mixtures thereof with other hydrocarbons to aromatics.

The present invention relates to an improved aromatization process wherein n-$C_6^+$ paraffinic and olefinic hydrocarbons, especially the latter, are converted to aromatic compounds by contacting a hydrocarbon feed stream containing such compounds with a catalyst comprising from about 0.05 to about 5% by weight of palladium metal and from about 0.1 to less than 2% by weight of chromium oxides composited with a high surface area support, and preferably with a catalyst which includes 0.05 to about 5% by weight of palladium metal, from about 0.1 to less than 2% by weight of chromium oxides and up to about 4.5% by weight of an alkali metal oxide. Catalyst compositions of the present invention comprise 0.05 to about 5% by weight of palladium metal, from about 0.1 to less than 2% by weight of chromium oxides and from about 0.01 to about 4.5% by weight of alkali metal oxide. Catalysts containing chromium oxide in concentrations ranging above about 2% possess relatively low activity for the dehydrocyclization of olefin feeds. This is probably due to excessive cracking and polymerization, resulting in carbon deposition on catalytic surfaces. The most active catalyst is produced when the alkali metal oxide is added to the catalyst. A catalyst which contains the triumvirate of metals (i.e., palladium, chromium and alkali metal) is far more effective for dehydrocyclization of n-$C_6^+$ olefins than any combination which excludes any one of these metals.

A more complete understanding of the present invention will be obtained from the following detailed disclosure and drawing wherein:

The FIGURE is a graph showing the variation in relative activity of a 0.5% Pd—0.5% $Cr_2O_3$—$Al_2O_3$ catalyst containing various amounts of $K_2O$ for hexene-1 aromatization at 850°F.

The catalyst supports employed in the present invention can be any support which affords high surface area. Generally, high surface area supports are those exhibiting surface areas ranging from about 50 m²/gm. to 1200 m²/gm. and preferably ranging from about 100 m²/gm. to 1200 m²/gm. Suitable supports can be selected from such materials as activated carbon or refractory inorganic oxides such as alumina, silica, zirconia, magnesia, titania, boria, strontia, hafnia and mixtures of two or more of such materials including silica-alumina, silica-zirconia, silica-magnesia, silica-titania, alumina-zirconia, alumina-magnesia, alumina-titania, magnesia-zirconia, titania-zirconia, magnesia-titania, silica-alumina-zirconia, silica-alumina-magnesia, silica-alumina-titania, silica-magnesia-zirconia, silica-alumina-boria and the like. The inorganic oxide supports can be prepared by precipitation of the hydrous oxide from aqueous solution. For example, hydrous aluminum oxide can be prepared by neutralization of an aluminum-containing solution. Another method of preparation involves the hydrolysis of the metal alkoxide(s). Alkoxides of aluminum, titanium and the like or mixtures thereof wherein the alkoxide groups each can contain from about 2 to about 5 carbon atom can be conveniently hydrolyzed in a one-step procedure by contacting the alkoxides with neutral water or aqueous alcohol solutions at a temperature of from about room temperature to about 200°F. After hydrolysis, the support can be recovered for subsequent impregnation as described in more detail below. Although impregnation can be effected directly on the filtered product, it is considered preferable to dry and calcine the support prior to impregnation. The calcination can be effected for periods of time ranging from 2 to about 20 hours.

The oxides of chromium are impregnated onto the support in critical concentration ranging from about 0.1 to less than 2% by weight, based on total catalyst.

The catalyst supports are further composited with palladium metal by treatment with a solution of a palladium metal salt, acid or ammonium complex, for example, ammonium chloropalladinate, chloropalladic acid, ammoniacal palladium chloride and the like. The amount of palladium metal in the final catalyst is generally between about 0.05 to about 5.0% by weight.

Impregnation of the catalyst support with the chromium oxides and the palladium salts, acids or ammonium complexes permits a much greater percentage of the metal oxide or salt to participate in the catalytic reaction than would be possible if the aforementioned salts were coprecipitated or cohydrolyzed with the support. Impregnation of the support can be conveniently accomplished by immersing the support in an aqueous solution of a mixture of the chromium oxides or derivatives thereof which can be subsequently oxidized to the oxide during calcination and a palladium metal salt, acid salt or ammonium complex. If desired, instead of impregnation of the support in a mixture of the palladium and chromium metal salts, the supports can be sequentially immersed in separate solutions of the different salts. One technique found especially useful in impregnation is the incipient wetness technique.

In this method, it is predetermined what volume of water is just sufficient to moisten the support uniformly and yet not have any extraneous liquid phase present. Knowing this volume, the liquid solution containing the metal oxide or derivative thereof or metal salt is made up in sufficient volume so that when applied to the support, a uniformly moistened, consistent paste results. Thereafter, the paste is dried at temperatures of about 300°F.

Once the supports have been impregnated and dried, they are calcined in air at temperatures ranging from about 800° to about 1200°F. for a period of time ranging from about 2 hours to about 20 hours.

To form a more active catalyst, pursuant to the practice of the present invention, a solution of an alkali metal oxide or a derivative thereof which can be subsequently oxidized to the oxide is employed to impregnate the dry calcined catalyst employing, for example, the incipient wetness technique described above. Any alkali metal oxide or oxidizable salt thereof can be suitably employed; thus, compounds of the metals of Group IA of the Periodic Table such as salts of lithium, sodium, potassium, rubidium, cesium, and francium can be used. Illustrative of such alkali metal compounds are potassium hydroxide, cesium oxide, potassium nitrate, sodium nitrate and the like. It is considered critical in the present invention that the amount of alkali metal oxide in the finished catalyst ranges from about 0.01 to about 4.5 and preferably from about 0.06 to 3.0 weight percent of the alkali metal oxide. The critical nature of the amount of alkali metal compounds as reflected in the relative activity of the catalyst for aromatization is graphically shown in the drawing which relates the variation in relative activity of a 0.5% Pd—0.5% $Cr_2O_3$—$Al_2O_3$ catalyst containing various amounts of $K_2O$ for hexene-1-aromatization at 850°F. It can be seen that above about 1.5% $K_2O$, there is a sharp drop-off in the relative activity of the catalyst. Other metal oxides of Group IA such as $Li_2O$, $Na_2O$, $Rb_2O$, $Cs_2O$, $Fr_2O$, can also be used. It is to be realized that to obtain the same amount of oxide on a molar basis, different weight percents of the other oxides need to be used. Thus, 1.5% $K_2O$ corresponds to about 0.4% $Li_2O$ or about 4.5% $Cs_2O$.

Once the catalyst has been impregnated with the alkali metal oxide, it is again calcined in air to temperatures ranging from about 800° to about 1200°F. for a period of time ranging from about 2 to about 20 hours to obtain the improved aromatization catalyts of the percent invention.

Although any inorganic oxide base or activated carbon can be suitably employed as a support for the catalyst of the present invention, it has been found that activation of the catalyst with alkali metal oxides is principally effective with the inorganic oxide bases since the activation effect obtained with alkali metal oxides is not currently particularly discernible when activated carbon bases are employed.

The aromatization process of the present invention is especially effective in converting n-$C_6^+$ paraffins and olefins, particularly the latter, to aromatics. The process can be employed with feedstreams which contain paraffins and/or olefins and diolefins, cycloolefins and naphthenes, or with mixed refinery streams such as a virgin or cat naphthas or heavier petroleum fractions.

The aromatization process is generally conducted at temperatures ranging from about 600° to about 1200°F. and preferably from about 800° to about 1050°F. Pressures in the range of 0 to 300 psig can be employed. This pressure can be autogenous or can be supplied by the addition of another gaseous substance. Since molecular hydrogen is a product of the reaction, it is sometimes preferred to employ inert gases such as nitrogen, methane, helium and the like. However, low pressures of hydrogen, up to about 200 psig, can be employed to suppress coke formation and prolong catalyst life. The hydrocarbon feed can be fed, upflow or downflow, through a fixed-bed or fluidized solids reactor feed rates ranging from about 0.01 to 10, and preferably from about 0.1 to 2 W/Hr./W. It is within the scope of this invention to adjust these operating variables such as temperature, pressure, feed rate, gas and the like to secure the optimum conversion to aromatics for the particular feed employed.

The catalyst can be periodically regenerated by heating the same to from about 800° to about 1200°F. for a period of time sufficient to burn deposited carbon off the catalyst. Generally, regeneration time can range from about 2 to about 20 hours. After regeneration, the catalyst can be reused.

It has been found that the catalysts of the present invention exhibit effective aromatization activity for a significant period of time. Thus, long cycle times within the reactor can be tolerated without adverse effect on aromatic conversion activity.

Thus, the catalysts of the present invention provide an effective means of converting the paraffin and/or olefin components of mixed refinery streams or in segregated olefin or paraffin streams to aromatic components thereby significantly enhancing the octane rating of the resulting gasoline or providing valuable blending components for gasoline because of their very high octane number.

The following series of nonlimiting examples and comparative demonstrations illustrate the more salient features of the invention, particularly the outstanding properties possessed by a catalyst composition which includes palladium, chromium oxides and an alkali metal oxide, in certain critical concentrations on a high surface area support, for aromatization of feeds which contain mixtures of n-$C_6^+$ paraffins and olefins (i.e., those containing hydrocarbon molecules providing a sufficient number of normally aligned carbon atoms, i.e., $C_6$ or greater, for direct rearrangement into aromatic compounds), particularly olefinic feeds, without the use of excessive amounts of hydrogen, if any.

For use in the reactions exemplified by the several examples and demonstrations, a catalyst support was prepared by hydrolyzing aluminum sec.-butoxide at 170° to 190°F. using a neutral aqueous solution of isopropanol (65–70% by weight isopropanol). The support was then respectively filtered, washed and preliminarily dried at 300°F. Thereafter, the support was calcined in air at 1000°F. for a period of 16 hours. The resultant calcined support, which exhibited a surface area of 242 $m^2$/gm and a pore volume of 1.5 cc./gm, was then divided into several portions and then used to make a series of catalysts.

Various combinations of the metals were then incorporated into different portions of the calcined support, to form the series of catalysts described hereafter, by use of the previously described incipient wetness technique using aqueous solutions of mixtures of an oxide or salt, or both, of the respective metal to be impregnated into the support. The resulting paste was dried at about 300°F. and then calcined at 1000°F. for 16 hours prior to testing for aromatization activity. After calcination, about 1 gm portions of catalyst were packed into nominal ¼ inch stainless steel tube reactors which were placed in sandbaths maintained at 850°F. Nitrogen gas was passed over the catalysts at 40 cc./minute. The gas was then changed to $H_2$ and the catalyst reduced for one hour at 1 atmosphere pressure and 850°F. The hydrogen was then flushed from the system with nitrogen gas at 40 cc./minute. Then, the nitrogen was diverted through a saturator containing hexene-1 at 32°F.

The following exemplifies the unique activity of a catalyst comprising palladium admixed with a small quantity of chromium oxide vis-a-vis catalysts constituted of the singular metal components, and also prevents a comparison with a platinum catalyst, known to be an outstanding catalyst in reforming reactions.

EXAMPLE 1

A series of runs was first conducted with catalysts (a) 0.5% $Cr_2O_3$—$Al_2O_3$, (b) 0.5% Pd—$Al_2O_3$, (c) 0.5% Pt—$Al_2O_3$, and (d) 0.5% Pd—0.5% $Cr_2O_3$—$Al_2O_3$ for aromatization of hexene-1, the reactions having been conducted in the absence of hydrogen at 850°F., 1 atmosphere $N_2$ and at a feed rate of hexene-1 of approximately 0.7 W/Hr./W for 2-hour cycle times. The product streams were analyzed by gas chromatographic techniques. The results obtained are all summarized in Table I.

TABLE I

AROMATIZATION OF HEXENE-1 AT 850°F., 1 ATM. $N_2$ AND 2 HR. CYCLE TIME

| Catalyst | 0.5% $Cr_2O_3$-$Al_2O_3$ | 0.5% Pd-$Al_2O_3$ | 0.5% Pt-$Al_2O_3$ | 0.5% Pd-0.5% $Cr_2O_3$-$Al_2O_3$ |
|---|---|---|---|---|
| W/Hr./W | 0.614 | 0.629 | 0.623 | 0.675 |
| Product Composition | | | | |
| Wt.% Cracked Products | 4.51 | 3.34 | 14.92 | 1.9 |
| Wt.% Hexenes | 95.49 | 89.57 | 84.92 | 69.32 |
| Wt.% Benzene (C) | 0 | 7.09 | 0.16 | 28.75 |
| Wt.% Benzene (Corr. to 0.7 W/Hr./W) | 0 | 6.40 | 0.14 | 27.89 |
| Wt.% Carbon on Catalyst | 0.31 | 4.11 | 3.07 | 4.11 |

From these data it will be observed that $Cr_2O_3$, Pd and Pt composited with alumina do not provide suitable aromatization catalysts but, in sharp contrast, palladium in combination with a small amount of chromium oxide provides a catalyst quite suitable for this purpose. Thus, 0.5% $Cr_2O_3$—$Al_2O_3$ catalyst is not active under these conditions for converting hexene-1 to benzene. Cracking is the only reaction. With the 0.5% Pd—$Al_2O_3$ catalyst, both cracking and aromatization occur, but only a small amount of aromatization occurs. The results obtained with the 0.5% Pt—$Al_2O_3$ show severe cracking, and virtually no aromatization. The presence of both chromium and palladium on a high surface area support are required to reduce cracking and produce high aromatization. Thus, this catalyst shows a conversion of hexene-1 to benzene of about 28%, with minimum cracking.

These data are also contrasted with those given in the following Table II, showing typical results obtained with prior art high $Cr_2O_3$ content (i.e., >2%) catalysts for aromatization of hexene-1 in the absence of hydrogen, at even higher temperatures at near atmospheric pressure.

TABLE II

CONVERSION OF HEXENE-1 TO AROMATICS (0.7 W/Hr/W using $N_2$ Carrier Gas)

| Catalyst | 10% $Cr_2O_3$ on $TiO_2$ | 10% $Cr_2O_3$-72% $TiO_2$-18% $Al_2O_3$ | 9% $Cr_2O_3$-1.5% $K_2O$-$Al_2O_3$ | 12% $Cr_2O_3$-$Al_2O_3$ | 12% $Cr_2O_3$-$Al_2O_3$ |
|---|---|---|---|---|---|
| Temp., °F. | 900 | 900 | 900 | 900 | 1000 |
| Product Comp., Wt.% on Feed | | | | | |
| Cracked | 0 | 1.5 | 0 | 4.7 | 13.8 |
| Benzene | 0.32 | 10.8 | 1.85 | 14.3 | 25.3 |

Appreciable conversion was only obtained at 1000°F. where considerable loss of feed to cracked products was encountered.

It is thus apparent that high chromium oxides content per se cannot account for the high aromatization activity of the catalysts of my invention.

Whereas conventional $Cr_2O_3$—$Al_2O_3$ catalysts, and catalysts loaded with a single metal (i.e., Group VIII or chromium) provide poor aromatization catalysts, at best, and whereas palladium in combination with chromium oxide produces a synergistic effect, nonetheless the activity of the latter is further enhanced by combining therewith small and critical amounts of an alkali metal oxide. the following example demonstrates a Pd—$Cr_2O_3$.$Al_2O_3$ catalyst to which is added small and critical amounts of $K_2O$.

EXAMPLE 2

A catalyst was prepared comprising 0.5% Pd—0.5% $Cr_2O_3$—$Al_2O_3$. Samples of this catalyst were segregated and each sample was impregnated with a varying amount of potassium nitrate by the incipient wetness technique and then calcined at 1000°F. to impart a finite amount of $K_2O$ to the final catalyst composition. These catalysts were evaluated for aromatization activity as described in Example 1 employing hexene-1 at 850°F. at 1 atm. nitrogen over a 2-hour cycle time. Table III summarizes the results obtained and illustrates the effect and criticality of the alkali metal oxide content.

As $K_2O$ is added via impregnation with $KNO_3$, the cracking activity decreases and disappears at the 0.5% level. At the same time, the conversion to benzene has nearly doubled. The amount of carbon deposited on the catalyst has decreased from about 4 to about 1 wt.%. Increases in $K_2O$ content beyond about 0.5 to 0.75% lowers the carbon forming tendency still further, but a sharp decrease in aromatization occurs. The various conversions obtained are expressed on a rate constant basis and relative activities have been assigned thereto. The criticality of $K_2O$ content can be more clearly seen by referring to the drawing wherein the data obtained herein are shown graphically.

TABLE III

EFFECT OF $K_2O$ CONTENT ON ACTIVITY OF 0.5% Pd—0.5% $Cr_2O_3$—$Al_2O_3$
AROMATIZATION OF HEXENE-1 AT 850°F., 1 ATM. $N_2$ AND 2 HR. CYCLE TIME

| Wt.% $K_2O$ | 0 | 0.2 | 0.5 | 0.75 | 1.0 | 1.5 | 5.0 |
|---|---|---|---|---|---|---|---|
| W/Hr./W | 0.675 | 0.678 | 0.717 | 0.686 | 0.661 | 0.657 | 0.682 |
| Product Composition | | | | | | | |
| Wt.% Cracked Products | 1.93 | 0.22 | 0 | 0 | 0 | 0 | 0 |
| Wt.% Hexenes | 69.32 | 59.83 | 52.45 | 48.83 | 56.20 | 71.20 | 98.25 |
| Wt.% Benzene (C) | 28.75 | 39.95 | 47.55 | 51.17 | 43.80 | 28.80 | 1.75 |
| Log $\frac{100}{100-C}$ (at 0.7 W/Hr./W) | 0.1420 | 0.2145 | 0.2871 | 0.3118 | 0.2364 | 0.1384 | 0.0075 |
| Wt.% Benzene (at 0.7 W/Hr./W) | 27.89 | 38.98 | 48.37 | 50.47 | 41.98 | 27.29 | 1.71 |
| Wt.% Carbon on Catalyst | 4.11 | 2.61 | 1.14 | 0.82 | 0.88 | 0.11 | 0.33 |
| Relative Activity+ | 100 | 151 | 202 | 220 | 166 | 97 | 12 |

EXAMPLE 3

Employing the procedure previously described, catalysts were prepared comprising 0.5% palladium and 0.5% chromium oxide on alumina. Samples of this catalyst were activated by treatment in one instance with 0.5% potassium oxide and in another instance with 1.5% cesium oxide in the manner described in Example 2. The activated catalysts were evaluated for the aromatization of hexene-1 at 850°F. and 1 atm. of nitrogen over a 2-hour cycle time. The results obtained are summarized in Table IV.

TABLE IV

EFFECT OF ALKALI METAL OXIDE ON ACTIVITY OF 0.5% Pd—0.5% $Cr_2O_3$-$Al_2O_3$

AROMATIZATION OF HEXENE-1 AT 850°F., 1 ATM. $N_2$ AND 2 HR. CYCLE TIME

| Alkali Metal Oxide | 0.5% $K_2O$ | 1.5% $Cs_2O$ |
|---|---|---|
| W/Hr./W | 0.717 | 0.597 |
| Product Compositions | | |
| Wt.% Cracked Products | 0 | 0 |
| WT.% Hexenes | 52.45 | 50.67 |
| Wt.% Benzene (C) | 47.55 | 49.33 |
| Log $\frac{100}{100-C}$ (at 0.7 W/Hr./W) | 0.2871 | 0.2518 |
| Wt.% Benzene (at 0.7 W/Hr./W) | 48.37 | 44.0 |
| Wt.% Carbon on Catalyst | 1.14 | 0.86 |

At a relatively low temperature of 850°F., the percent conversion to benzene was at least 44%. No cracking occurred and the amount of carbon amounted to, at most, 1.14%. It can be seen that both alkali metal oxides effectively enhance the aromatization activity of the catalysts as compared with the data contained in Table I.

EXAMPLE 4

Employing the procedure described in Example 2, a catalyst was prepared comprising 0.5% Pd—0.5% $Cr_2O_3$—1.5% $K_2O$—$Al_2O_3$. This catalyst was evaluated for aromatization activity employing hexene-1 at 850°F. over a 2-hour cycle time. In one run, 1 atm. of nitrogen was employed whereas in another run 1 atm. of hydrogen was employed. Table V below summarizes the results obtained and illustrates that the presence of hydrogen can suppress the aromatization reaction for hexene-1 at 850°F.

TABLE V

EFFECT OF HYDROGEN PRESSURE ON ACTIVITY OF 0.5% Pd—0.5% $Cr_2O_3$—1.5% $K_2O$—$Al_2O_3$
AROMATIZATION OF HEXENE-1 AT 850°F., AND 2 HR. CYCLE TIME

| Gas Pressure | 1 Atm. $N_2$ | 1 Atm. $H_2$ |
|---|---|---|
| W/Hr./W | 0.657 | 0.724 |
| Product Composition | | |
| Wt.% Cracked Products | 0 | 0 |
| Wt.% Hexenes | 71.20 | 100 |
| Wt.% Benzene (C) | 28.80 | 0 |
| Log $\frac{100}{100-C}$ (at 0.7 W/Hr./W) | 0.1384 | 0 |
| Wt.% Benzene (at 0.7 W/Hr./W) | 27.29 | 0 |
| Wt.% Carbon on Catalyst | 0.11 | 0.27 |

It can be seen that pressures of as much as 1 atmosphere hydrogen can suppress the aromatization activity.

With feeds that are inherently more difficult to aromatize such as actual refinery streams, higher temperatures than 850°F. are desired. Under these conditions, more hydrogen pressure can be tolerated. This is sometimes advantageous since coke make can be reduced and catalytic activity can be maintained for a longer period of time with some hydrogen pressure. It is to be understood that depending on feedstock and temperature, an optimum minimum hydrogen pressure will exist.

EXAMPLE 5

Employing a catalyst comprising 0.5% Pd—0.5% $Cr_2O_3$—$Al_2O_3$, an aromatization reaction was conducted using a 200°–335°F. catalytic naphtha. Results are given in Table VI.

TABLE VI

AROMATIZATION OF A 200-335°F. CAT NAPHTHA ON 0.5% Pd-0.5% $Cr_2O_3$ ON $Al_2O_3$ AT 950°F., 10 PSIG, 1 V/V/HR. AND 2-HR. CYCLE TIME

| Gas Used Composition, Wt.% on Feed | Feed Analysis | $N_2$ | $H_2$ (820 SCF/Bbl.) |
|---|---|---|---|
| $C_5^-$ | — | 2.7 | 9.8 |
| Alkylbenzenes | 28.0 | 51.1 | 46.1 |
| Polycyclics | 2.3 | 2.5 | 2.8 |
| Isoparaffins | 12.3 | 9.2 | 9.6 |
| n-Paraffins | 7.7 | 6.4 | 7.2 |
| Cyclic $C_5$ | 8.6 | 6.2 | 7.0 |
| Cyclic $C_6$ | 8.8 | 5.6 | 6.7 |
| Olefins | 15.7 | 5.7 | 5.2 |
| Cycloolefins | 16.6 | 1.9 | 1.2 |
| Carbon | — | 7.8 | 4.5 |

With this refinery stream, it can be seen that the alkylbenzenes were increased from 28 to 51% using the catalyst and process of this invention. The amount of olefins and cyclo(or di) olefins was substantially reduced. In the run using hydrogen, only a somewhat lower conversion to 46% alkylbenzenes was obtained but the carbon production was substantially decreased.

EXAMPLE 6

Employing a catalyst comprising 0.5% Pd—0.5% $Cr_2O_3$—0.5% $K_2O$—$Al_2O_3$ prepared as described in Example 2, an aromatization reaction was conducted employing hexene-1 at 1 atm. of nitrogen over a 2-hour cycle time. The reaction temperature was varied and the product composition obtained at each temperature was recorded. The results obtained are summarized in Table VII below.

TABLE VII

EFFECT OF REACTION TEMPERATURE AROMATIZATION OF HEXENE-1 ON 0.5% Pd-0.5% $Cr_2O_3$-0.5% $K_2O$-$Al_2O_3$ (2-HR. CYCLE TIME; 1 ATM. $N_2$)

| | | | | |
|---|---|---|---|---|
| Reduction (1 atm. $H_2$), Hr./°F. | 1/800 | 1/850 | 1/875 | 1/900 |
| W/Hr./W | 0.662 | 0.717 | 0.675 | 0.668 |
| Reaction Temp., °F. | 800 | 850 | 875 | 900 |
| Product Composition | | | | |
| Wt.% Cracked Products | 0 | 0 | 0 | 0 |
| Wt.% Hexenes | 79.18 | 52.45 | 30.4 | 31.4 |
| Wt.% Benzene | 20.82 | 47.55 | 69.6 | 68.6 |
| Wt.% Benzene (at 0.7 W/Hr./W) | 19.82 | 43.37 | 68.28 | 66.90 |
| Wt.% Carbon on Catalyst | — | 1.14 | 1.18 | 1.41 |

It can be seen that at temperatures ranging from 800° to 900°F., conversions to benzene increase from 19.8% to 66.9%. It also can be seen that the activity of the catalyst begins to flatten above about 875°F.

EXAMPLE 7

A catalyst base was prepared by hydrolyzing a mixture of aluminum sec.-butoxide and titanium isopropoxide. This base consisted of 67% $Al_2O_3$ and 33% $TiO_2$ and had a surface area of 327 m²/gm. 0.5% Pd and 0.5% $Cr_2O_3$ were impregnated on this support by the method described in Example 1. This material also showed high activity for converting hexene-1 to aromatics as shown in Table VIII.

TABLE VIII

AROMATIZATION OF HEXENE-1 ON 0.5% Pd-0.5% $Cr_2O_3$-33% $TiO_2$-67% $Al_2O_3$

| | |
|---|---|
| W/Hr./W | 0.606 |
| Reaction Temp., °F. | 850 |
| Product Composition | |
| Wt.% Cracked Products | 5.7 |
| Wt.% Hexenes | 63.7 |
| Wt.% Benzene | 30.6 |
| Wt.% Benzene (at 0.7 W/Hr./W) | 27.1 |

EXAMPLE 8

Activated charcoal (1183 m²/gm) manufactured by Columbia Carbon Company was substituted in lieu of the alumina support. Catalysts were prepared containing 0.5% palladium on the activated charcoal, 0.5% Pd—0.5% $Cr_2O_3$ on the activated charcoal, and 0.5% Pd—0.5% $Cr_2O_3$—0.5% $K_2O$ on the activated charcoal by the manner described in Examples 1 and 2. These catalysts were evaluated for aromatization activity employing hexene-1 in 1 atm. nitrogen over a 2-hour cycle time. The results obtained are summarized in Table IX.

TABLE IX

AROMATIZATION OF HEXENE-1 ON CHARCOAL BASED CATALYSTS (2 HR. CYCLE TIME, 1 ATM. $N_2$)

| Catalyst | 0.5% Pd-Char. | 0.5% Pd-Char. | 0.5% Pd-0.5% $Cr_2O_3$-Char | 0.5% Pd-0.5% $Cr_2O_3$-0.5% $K_2O$-Char. |
|---|---|---|---|---|
| W/Hr./W | 0.597 | 0.546 | 0.595 | 0.578 |
| Temp., °F. | 850 | 950 | 850 | 850 |
| Product Composition | | | | |
| Wt.% Cracked Prod. | 4.43 | 21.43 | 4.28 | 4.10 |
| Wt.% Hexenes | 80.57 | 48.66 | 48.43 | 75.89 |
| Wt.% Benzene | 15.00 | 29.91 | 47.29 | 20.01 |
| Wt.% Benzene (at 0.7 W/Hr./W) | 12.95 | 24.22 | 41.98 | 16.84 |

It can be seen that the Pd—$Cr_2O_3$-charcoal catalyst exhibits somewhat higher activity than the corresponding alumina-based catalyst for aromatizing hexene-1 (see Table I). The combination of Pd—$Cr_2O_3$ on charcoal shows a synergistic effect analogous to that on alumina. At 850°F., a conversion to benzene of 42% is obtained which is twice that of the Pd-charcoal catalyst at the higher temperature of 950°F. It can be seen, however, that the addition of $K_2O$ does not exhibit an activating effect on charcoal as it does with alumina based catalyst with respect to aromatization activity.

EXAMPLE 9

The aromatization activity of catalysts prepared in Examples 1 and 2 was further compared to a conventional reforming catalyst containing 0.3% Pt on $Al_2O_3$. The aromatization reactions were conducted with hexene-1 at 900°F. The results are summarized in Table X.

TABLE X

AROMATIZATION OF HEXENE-1 AT 900°F., 1 ATM. $N_2$ AND 2 HR. CYCLE TIME

| Catalyst | 0.3% Pt-$Al_2O_3$ | 0.5% Pd-0.5% $Cr_2O_3$-$Al_2O_3$ | 0.5% Pd-0.5% $Cr_2O_3$-1.5% $K_2O$-$Al_2O_3$ |
|---|---|---|---|
| W/Hr./W | 0.628 | 0.639 | 0.629 |
| Product Composition | | | |
| Wt.% Cracked Products | 13.0 | 3.6 | 0 |

TABLE X-continued

AROMATIZATION OF HEXENE-1 AT 900°F.,
1 ATM. $N_2$ AND 2 HR. CYCLE TIME

| Catalyst | 0.3% Pt-$Al_2O_3$ | 0.5% Pd-0.5% $Cr_2O_3$-$Al_2O_3$ | 0.5% Pd-0.5% $Cr_2O_3$-1.5% $K_2O$-$Al_2O_3$ |
|---|---|---|---|
| Wt.% Hexenes | 86.8 | 54.2 | 34.0 |
| Wt.% Benzene (C) | <1.0 | 42.2 | 66.0 |
| Wt.% Benzene (at 0.7 W/Hr./W) | <0.89 | 39.4 | 64.4 |
| Wt.% Carbon on Catalyst | 2.93 | 4.97 | 0.56 |

It can be seen that the Pt—$Al_2O_3$ catalyst is essentially inactive at these conditions. The 0.5% Pd—0.5% $Cr_2O_3$—$Al_2O_3$ not only gives high conversion to benzene of 39.4% but also gives much less cracking. Incorporation of $K_2O$ further increases conversion to benzene to 64.4% with no cracking and substantially reduced carbon make.

In many of the examples shown in this invention, the catalysts have been pre-reduced with hydrogen at the temperature of the subsequent run. This step although desirable is not necessary to produce highly active catalysts since the hydrogen produced in situ during the aromatization reaction is sufficient for reduction of the catalyst.

It is within the scope of this invention to employ the Pd—$Cr_2O_3$—$K_2O$—$Al_2O_3$ system as part of a petroleum process involving the reforming of petroleum streams to produce high octane motor gasolines in which the octanes are obtained by increasing aromatic and isoparaffinic content. For example, it is contemplated that a petroleum stream is first contacted with a conventional reforming catalyst such as Pt—$Al_2O_3$ at mild conditions to convert primarily the cycloparaffins to aromatics. This stream is then passed through a bed containing the catalyst of this invention at higher temperatures to convert primarily the straight chain hydrocarbons to aromatics. The presence of $K_2O$ on the catalyst prevents excessive loss of feed to cracked products in this second stage.

Although specific materials and conditions were set forth in the above exemplary processes in making and using the aromatization catalyst of this invention, these are merely intended as illustrations of the present invention. Various other feed streams, supports, catalyst constituents and process conditions such as those listed above may be substituted in the examples with similar results.

Other modifications of the present invention will occur to those skilled in the art upon a reading of the present disclosure. These are intended to be included within the scope of this invention.

Having described the invention, what is claimed is:

1. Process for the preparation of aromatic hydrocarbons from a feedstream containing n-$C_6^+$ hydrocarbons selected from the group consisting of paraffins, olefins and mixtures thereof comprising contacting said feedstream in a reaction zone maintained at temperatures ranging from about 600° to about 1200°F. and at pressures ranging from about 0 to about 300 psig with a catalyst consisting essentially of from about 0.05 to about 5% of palladium metal, from about 0.1 to less than 2% chromium oxides, and from about 0.01 to about 4.5% by weight of an alkali metal oxide promoter, on a high surface area support.

2. Process as defined in claim 1 wherein the support is a refractory inorganic oxide or a mixture of such inorganic oxides.

3. Process as defined in claim 2 wherein the support is alumina.

4. Process as defined in claim 2 wherein the support is $TiO_2$/$Al_2O_3$.

5. Process as defined in claim 1 wherein the support is an activated carbon support.

6. Process as defined in claim 1 wherein the catalyst contains thereon from about 0.06 to about 3.0% by weight of an alkali metal oxide.

7. Process as defined in claim 6 wherein the alkali metal oxide promoter is $K_2O$ which is present in amounts ranging up to about 1.5% by weight.

8. Process as defined in claim 6 wherein the alkali metal oxide is cesium oxide.

9. Process as defined in claim 1 wherein the hydrocarbon feedstream is contacted with the cataylst in a reaction zone maintained at temperatures ranging from about 800° to about 1050°F. and at pressures ranging from 0 to 200 psig.

10. Process as defined in claim 9 wherein the hydrocarbon conversion is conducted in the absence of added hydrogen.

11. Process as defined in claim 9 wherein the hydrocarbon conversion is conducted in the presence of an inert gas.

12. Process as defined in claim 9 wherein the hydrocarbon conversion is conducted in the presence of up to about 200 psig of hydrogen.

13. Process as defined in claim 9 wherein the hydrocarbon feed is fed to the reaction zone at feed rates ranging from about 0.01 to 10 W/Hr./W.

14. Process as defined in claim 9 wherein the hydrocarbon feedstream is an olefin-containing stream.

15. Process as defined in claim 9 wheren the hydrocarbon feed is a cat naphtha.

16. Process for the preparation of aromatic hydrocarbons from a feedstream containing hydrocarbons selected from the group consisting of n-$C_6^+$ paraffins, olefins and mixtures thereof comprising contacting said feedstream in a reaction zone maintained at temperatures ranging from about 600° to about 1200°F. and at pressures ranging from about 0 to about 300 psig with a catalyst consisting essentially of from about 0.05 to about 5% of palladium metal and from about 0.1 to less than 2% of chromium oxides, on a high surface area support.

17. An aromatization catalyst comprising from about 0.05 to about 5% by weight of palladium metal and from about 0.1 to less than 2% of chromium oxide impregnated on a support of surface area ranging from about 100 m²/g to 1200 m²/g, said catalyst being promoted with an effective amount of about 0.01 to about 4.5% by weight of an alkali metal oxide.

18. An aromatization catalyst as defined in claim 17 wherein the alkali metal oxide is present in amounts ranging from about 0.06 to about 3.0% by weight.

19. An aromatization catalyst as defined in claim 18 wherein the alkali metal oxide is potassium oxide, and the concentration thereof ranges up to about 1.5% by weight.

20. An aromatization catalyst as defined in claim 17 wherein the alkali metal oxide is cesium oxide.

21. An aromatization catalyst as defined in claim 16 wherein the high surface area support is an inorganic oxide and has a surface area ranging from about 100 m$^2$/g to about 1200 m$^2$/g.

22. An aromatization catalyst as defined in claim 17 wherein the support is alumina.

23. An aromatization catalyst as defined in claim 17 wherein the support is $TiO_2/Al_2O_3$.

24. An aromatization catalyst as defined in claim 17 comprising 0.5% palladium, 0.5% chromium oxide, 0.5% potassium oxide on the surface of an alumina support.

* * * * *